(12) United States Patent
Tanaka et al.

(10) Patent No.: US 7,589,323 B2
(45) Date of Patent: Sep. 15, 2009

(54) SUPERCONDUCTING X-RAY DETECTOR AND X-RAY ANALYSIS APPARATUS USING THE SAME

(75) Inventors: Keiichi Tanaka, Chiba (JP); Akikazu Odawara, Chiba (JP); Satoshi Nakayama, Chiba (JP)

(73) Assignee: SII NanoTechnology Inc. (JP)

( * ) Notice: Subject to any disclaimer, the term of this patent is extended or adjusted under 35 U.S.C. 154(b) by 163 days.

(21) Appl. No.: 11/794,288

(22) PCT Filed: Jan. 24, 2006

(86) PCT No.: PCT/JP2006/300987

§ 371 (c)(1),
(2), (4) Date: Aug. 2, 2007

(87) PCT Pub. No.: WO2006/078024

PCT Pub. Date: Jul. 27, 2006

(65) Prior Publication Data

US 2007/0291902 A1 Dec. 20, 2007

(30) Foreign Application Priority Data

Jan. 24, 2005 (JP) .............................. 2005-015179

(51) Int. Cl.
*H01L 27/18* (2006.01)

(52) U.S. Cl. .................. 250/310; 701/40; 701/132; 250/336.2

(58) Field of Classification Search .................... None
See application file for complete search history.

(56) References Cited

U.S. PATENT DOCUMENTS 4,970,395 A * 11/1990 Kruse, Jr. .................. 250/336.2
5,710,437 A * 1/1998 Kurakado et al. ............. 257/32
5,777,336 A * 7/1998 Silver et al. ............. 250/370.15
6,239,431 B1 * 5/2001 Hilton et al. .............. 250/336.2
6,648,503 B2 * 11/2003 Tanaka et al. .................. 374/31
6,786,632 B2 * 9/2004 Tanaka et al. .................. 374/31
6,907,359 B2 * 6/2005 Tanaka et al. .................. 702/40
7,241,997 B2 * 7/2007 Odawara et al. ......... 250/336.2

FOREIGN PATENT DOCUMENTS

JP  2000284054  10/2000
JP  2004226147  8/2004

* cited by examiner

*Primary Examiner*—David A Vanore
*Assistant Examiner*—Andrew Smyth
(74) *Attorney, Agent, or Firm*—Adams & Wilks

(57) ABSTRACT

To provide a superconducting X-ray detector capable of carrying out a measurement by a high energy resolution by restraining a reduction in a sensitivity by a self magnetic field. A superconducting X-ray detector comprising a temperature detector 6 for detecting a temperature change by heat generated when an X-ray is absorbed, and a heat link 3 for controlling a heat flow amount of escaping the generated heat to a support board i, wherein the temperature detector 6 comprises a heat conducting multilayer thin film, the superconducting X-ray detector is constituted by a structure of providing a superconductor layer 4 above the heat link 3 and providing an insulating member 2 between the superconductor layer 4 and the temperature detector 6, the superconductor layer 4 and the temperature detector 6 are connected by a superconducting wiring 7 and uses materials by which superconducting transition temperatures of the superconductor layer 4 and the superconducting wiring 7 are higher than a superconducting transition temperature of the temperature detector 6.

4 Claims, 3 Drawing Sheets

SUPERCONDUCTING X-RAY DETECTOR AND X-RAY ANALYSIS APPARATUS USING THE SAME

CROSS-REFERENCE TO RELATED APPLICATIONS

This application is a U.S. national stage application of International Application No. PCT/JP2006/300987, filed Jan. 24, 2006, claiming a priority date of Jan. 24, 2005, and published in a non-English language.

TECHNICAL FIELD

The present invention relates to a superconducting X-ray detector realizing a high energy resolution by using a temperature detector by absorbing an energy of an X-ray to be converted into heat and utilizing a transitional state between a superconducting state and a normal conducting state by the converted heat and an X-ray analysis apparatus using the same.

BACKGROUND ART

In a background art, there is known an energy dispersive spectroscopy (EDS) in an element analysis, an impurity inspection or the like using a semiconductor, which is characterized in capable of carrying out an element analysis in a short period of time in a wide energy range in the element analysis, the impurity inspection or the like. However, the energy resolution of the energy dispersive spectroscopy depends on an energy gap provided to the semiconductor, and therefore, the energy resolution cannot be made to be equal to or smaller than 100 eV.

Hence, a superconducting X-ray detector is expected as a detector promoting a function of an energy resolution and also having a function of a high counting rate.

For example, a superconducting transition edge sensor type calorimeter constituting one of a superconducting X-ray detector is referred to as TES (Transition Edge Sensor) since the calorimeter utilizes a superconducting transition edge producing a large resistance change relative to a small temperature change (hereinafter, described as TES).

TES comprises a temperature detector for sensing a temperature change by heat generated in accordance with absorption of an X-ray, and a heat link used for escaping the heat generated at inside of the temperature detector to a support board.

When an X-ray is incident on an absorbing member in a state of driving the temperature detector by a constant voltage, a temperature at inside of the temperature detector rises, and a resistance of the temperature detector is rapidly increased by the temperature rise. By increasing the resistance value, a value of a current flowing at inside of the temperature detector is reduced.

A relationship between a current displacement ($\Delta I$) by a reduction in the current value and an energy (E) of X-ray incident on TES can be expressed by the following equation.

[Equation 1]

$$E = \Delta I V_n \tau_{\mathit{eff}} \tag{1}$$

In the relationship, notation $V_n$ designates a drive voltage, notation $\tau_{\mathit{eff}}$ designates a time constant of a current pulse.

Therefore, the energy of the incident X-ray can be calculated by measuring the current displacement.

Further, an energy resolution ($\Delta E$) of TES can be expressed by the following equation.

[Equation 2]

$$\Delta E = 2.355 \xi \sqrt{K_B T^2 C} \tag{2}$$

In the equation, notation $K_B$ designates the Boltzmann constant, notation T designates an operational temperature, notation C designates a heat capacity, notation $\xi$ designates a parameter depending on a sensitivity of the superconducting X-ray detector, and when the sensitivity of the temperature detector is designated by notation $\alpha$, the following relationship is established.

$$\Delta E \propto \sqrt{(K_B T^2 C / \alpha)} \tag{3}$$

It is necessary therefrom that in order to promote the energy resolution, the sensitivity is increased and the operational temperature is reduced.

Here, the operational temperature is determined by a function of a refrigerator for cooling the superconducting X-ray detector, and a currently obtainable cooling function of a dilution refrigerator or an adiabatic demagnetization refrigerator is 50-100 mK. Therefore, a transition temperature of the temperature detector is set to be 100 mK-200 mK (refer to Nonpatent Reference 1).

Nonpatent Reference 1: K. D. Irwin and other 8 person, Superconducting transition-edge-microcalorimeter x-ray spectrometer with 2 eV energy resolution at 1.5 keV, "Nuclear Instruments and Methods in Physics research A", US, American Physics Society, 2000, 444, P. 145-150

DISCLOSURE OF THE INVENTION

Problems that the Invention is to Solve

However, in TES according to the background art, a magnetic field of the temperature detector per se (hereinafter, refer to as self magnetic field) is generated in accordance with Ampere's law by a current flowing in the temperature detector.

Further, there poses a problem that the sensitivity of the temperature detector is reduced by the self magnetic field.

As is apparent from equation (3), by reducing the sensitivity $\alpha$, the energy resolution is reduced.

In view of the problem of the background art, it is an object of the invention to provide a superconducting X-ray detector capable of measuring by a high energy resolution by restraining a reduction in a sensitivity by a self magnetic field.

Means for Solving the Problems

In order to resolve the above-described problem, the invention is a superconducting X-ray detector constituted by a temperature detector for detecting a temperature change by heat generated when an X-ray is absorbed, and a heat link for controlling a heat flow amount of escaping the generated heat to a support board, and the temperature detector being formed of the superconducting multilayer thin film, wherein the superconducting X-ray detector is constituted by a structure of providing a superconductor layer above the heat link and providing an insulating member between the superconductor layer and the temperature detector, and the superconductor layer and the temperature detector are connected by a superconducting wiring and superconducting transition temperatures of the superconductor layer and the superconducting wiring are higher than a superconducting transition temperature of the temperature detector.

Or, the invention is constituted by a structure of providing a superconductor layer above the heat link, providing an insulating member above the superconductor layer, and providing the temperature detector above the insulating member, and the superconductor layer and the temperature detector are connected by a superconducting wiring, and the superconductor layer and the superconducting multilayer thin film of the temperature detector are constituted by the same material.

ADVANTAGE OF THE INVENTION

According to the superconducting X-ray detector of the invention constituted as described above, directions of currents flowing in the temperature detector and the superconductor layer are reverse to each other, and therefore, also self magnetic fields generated from the temperature detector and the superconductor layer are directed in directions reverse to each other and cancelled by each other. Thereby, the reduction in a sensitivity of the temperature detector by the magnetic field applied to the temperature detector can be restrained and a measurement can be carried out by a high energy resolution.

DESCRIPTION OF REFERENCE NUMERALS AND SIGNS

Figure 1:
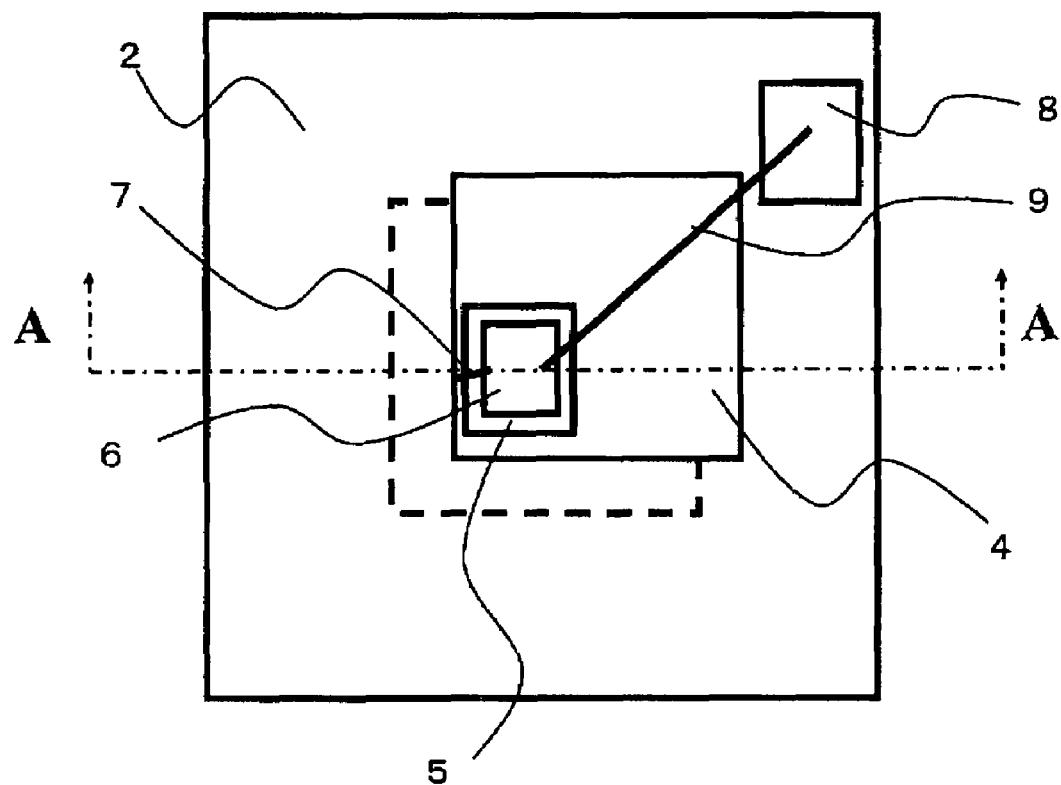
FIG. 1 is an outline view of a superconducting X-ray detector according to a first embodiment.

1 . . . support board
2 . . . heat link (insulating member)
3 . . . superconducting wiring
4 . . . superconductor layer
5 . . . insulating member
6 . . . temperature detector
7 . . . superconducting wiring
8 . . . superconducting terminal
9 . . . superconducting wiring
10 . . . superconductor layer
11 . . . superconducting terminal
100 . . . refrigerator
102 . . . superconducting X-ray detector
101 . . . cabinet
103 . . . cooling head
110 . . . sample chamber
111 . . . lens-barrel
112 . . . secondary electron detector
113 . . . sample stage
120 . . . sample

BEST MODE FOR CARRYING OUT THE INVENTION

Figure 2:
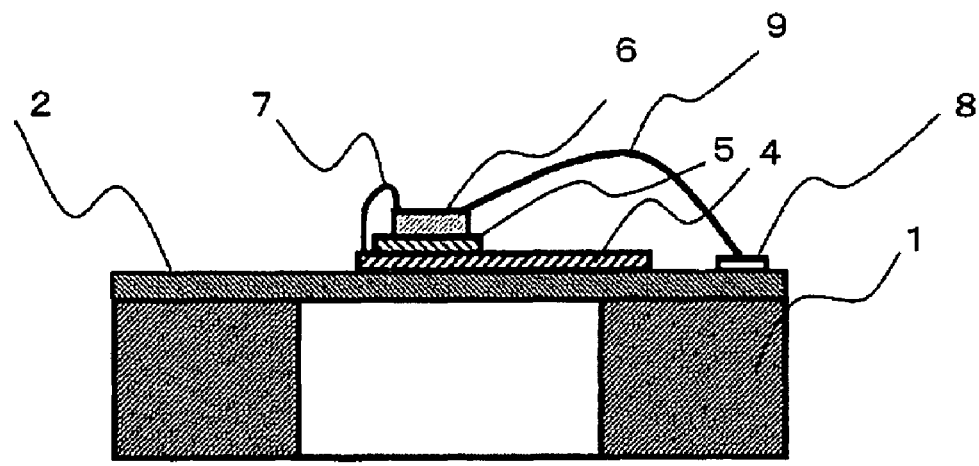
FIG. 2 is a sectional view of the superconducting X-ray detector according to the first embodiment.

As a first embodiment, FIG. 1 is an outline view viewed from above a superconducting X-ray detector according to Claim 1 of the invention, FIG. 2 is a sectional view taken along a line A-A shown in FIG. 1. The insulating member 2 is provided above the support board 1, a portion of the support board 1 is hollowed, and an insulating member a lower portion of which is hollowed is functioned as the heat link 2. Silicon is used as the support board 1, and there is, for example, silicon nitride or silicon oxide as a material of the insulating member. As the superconductor layer 4, there is used niobium having a transition temperature of about 9 K, the transition temperature being higher than that of the temperature detector 6, or aluminum having a transition temperature of about 1 K or the like is used. The insulating member 5 is provided above the superconductor layer 4. As the insulating member 5, silicone nitride, silicon oxide, or tantalum oxide, tantalum nitride is used. The temperature detector 6 is provided above the insulating member 5. As the temperature detector 6, for example, an Au/Ti thin film, an Au/Mo thin film, or an Au/Al thin film is used.

The superconducting wiring 7 is provided between an end portion of the temperature detector 6 and the superconductor layer 4, the superconducting wiring 9 is provided between an end portion on an opposed side of the temperature detector 7 and the superconducting terminal 8 provided above the support board 1 to be respectively electrically connected thereto.

Although according to the embodiment, the superconductor layer 4 is constituted by a shape of including a region above the support board 1 by way of the insulating member 2, the superconductor layer 4 may be constituted by a shape which is not included in the region above the support board 1.

When a dilution refrigerator or an adiabatic demagnetization refrigerator is used as a refrigerator for cooling the superconducting X-ray detector, the superconducting X-ray detector can be cooled to be equal to or lower than 100 mK. When the refrigerator is used, in order to promote the energy resolution, respective film thicknesses of materials of the temperature detector 6 are adjusted, and the transition temperature of the temperature detector 6 is constituted by 100-200 mK.

As materials of the superconducting terminal 8, the superconducting wiring 7 and the superconducting wiring 9, there is used, for example, niobium or aluminum which are materials having transition temperatures higher than that of the temperature detector 6.

Here, by constructing the constitution of the embodiment, directions of currents flowing in the temperature detector 6 and the superconductor layer 4 are constituted by directions reverse to each other, also self magnetic fields generated from the temperature detector 6 and the superconductor layer 4 are directed in directions reverse to each other to be operated in directions canceling each other. Therefore, a reduction in a sensitivity of the temperature detector by the magnetic field applied to the temperature detector can be restrained and a high resolution measurement can be carried out.

Further, by making the transition temperature of the superconductor layer 4 lower than the transition temperature of the temperature detector, the superconductor layer is always brought into a superconducting state by an operational temperature of the temperature detector, and therefore, an external magnetic field invading the temperature detector can be shielded by the superconducting member and a reduction in a sensitivity by the external magnetic field can also be restrained.

Figure 3:
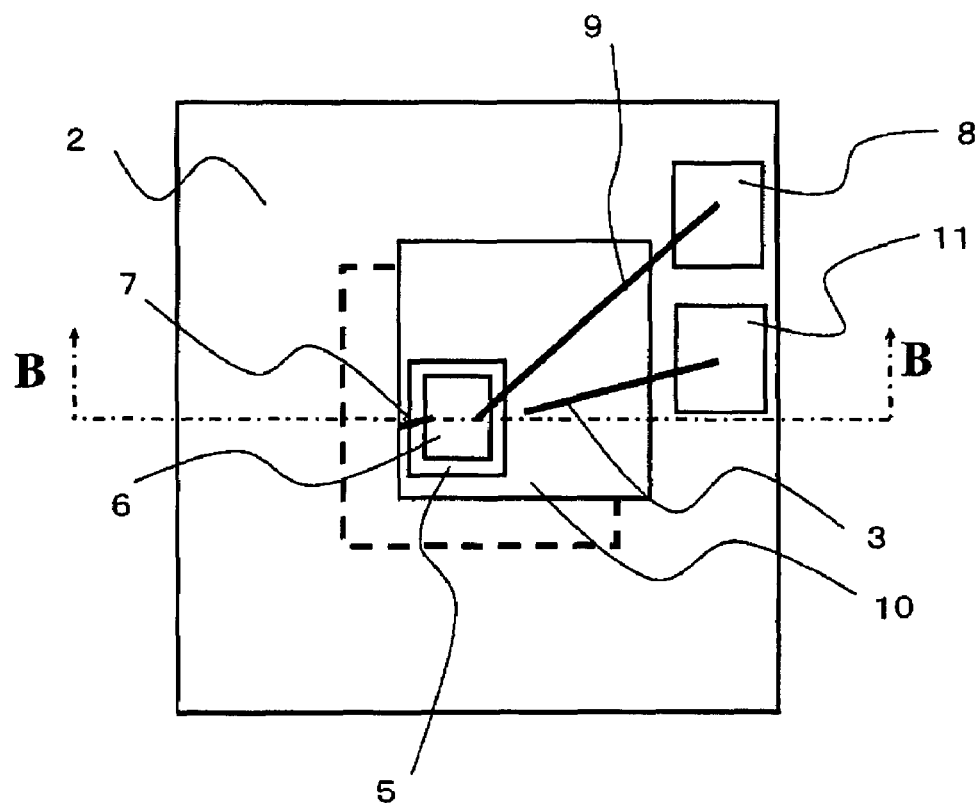
FIG. 3 is an outline view of a superconducting X-ray detector according to a second embodiment.
Figure 4:
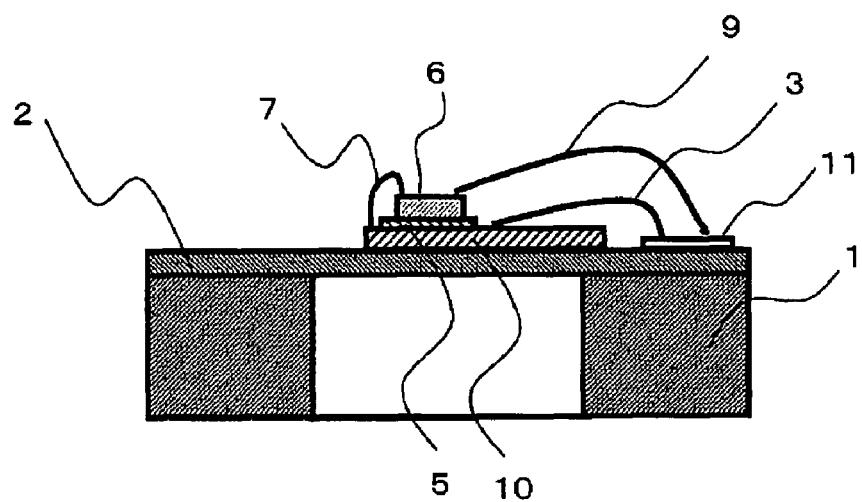
FIG. 4 is a sectional view of the superconducting X-ray detector according to the second embodiment.

Next, as a second embodiment, FIG. 3 is an outline view viewed from above a superconducting X-ray detector according to Claim 2 of the invention, FIG. 4 is a sectional view taken along a line B-B shown in FIG. 3. The insulating member 2 is provided above the support board 1, a portion of the support board 1 is hollowed, and the insulating member 2 a lower portion of which is hollowed is functioned as a heat link. The superconductor layer 10 comprising a superconducting multilayer thin film the same as that of the temperature detector 6 is formed above the insulating member 2, and the insulating member 5 is provided above the superconductor layer 10. The temperature detector 6 is provided above the insulating member 5. As the temperature detector 6, for example, an Au/Ti thin film, an Au/Mo thin film, or an Au/Al thin film is used. The superconducting wiring 7 is provided between an end portion of the temperature detector 6 and the superconductor layer 10, the superconducting wiring 9 is provided between an end portion on an opposed side of the temperature detector 7 and the superconducting terminal 8 provided above the support board 1, further, the superconducting wiring 3 is provided between an end portion on an opposed side of the superconductor layer 10 and the superconducting terminal 11 provided above the support board 1 to be respectively electrically connected thereto. A material constituting other than these is the same as that of the first embodiment.

Further, respective film thicknesses of materials of the temperature detector 6 and the superconductor layer 10 are adjusted, and transition temperatures of the temperature detector 6 and the superconductor layer 10 are made to be 100-200 mK.

Further, both in the first, the second embodiments, in order to promote an efficiency of absorbing a radiation, an absorbing member for promoting an efficiency of absorbing an X-ray may be provided at the temperature detector.

As materials of the superconducting terminals 8, 11 and the superconducting wirings 7, 9, 3, there is used a niobium having a transition temperature of about 9 K which is higher than that of the temperature detector 6, aluminum having a transition temperature of about 1 K or the like.

Thereby, directions of currents flowing in the temperature detector 6 and the superconductor layer 10 are constituted by directions reverse to each other, also self magnetic fields generated from the temperature detector 6 and the superconductor layer 10 are constituted by directions reverse to each other to be operated in directions of canceling each other. Thereby, a reduction in a sensitivity of the temperature detector by a magnetic field applied to the temperature detector 6 can be restrained and a high resolution measurement can be carried out.

Further, when an operational resistance of the temperature detector is designated by notation R, the current is designated by notation I, a thermal conductivity of the heat link is designated by notation G, the operational temperature of the temperature detector is designated by notation T, and a temperature of the support board is designated by Tb, a relationship of equation (7) is established.

$$I^2 R = G(T - T_b) \quad (7)$$

Since the superconductor layer 10 is constituted by the superconducting multilayer thin film the same as that of the temperature detector 6, an effective operational resistance becomes higher than R, and the current flowing in the temperature detector 6 by the superconductor layer 10 is reduced.

Thereby, also the self magnetic field generated at the temperature detector 6 by the superconductor layer 10 is reduced to be suitable for canceling the self magnetic fields by each other.

That is, when the respective self magnetic fields cannot be completely canceled by each other by the temperature detector 6 and the superconductor layer 10, by making intensities of the self magnetic fields generated from the temperature detector 6 and the superconductor layer 10 small, a difference between the intensities of the magnetic fields which cannot be canceled by each other can be reduced to thereby enable to restrain the reduction in the sensitivity.

Further, the superconductor layer 10 is operated for irradiation of the X-ray similar to the temperature detector 6, and therefore, there is also achieved an effect of promoting the efficiency of absorbing the incident X-ray.

Figure 5:
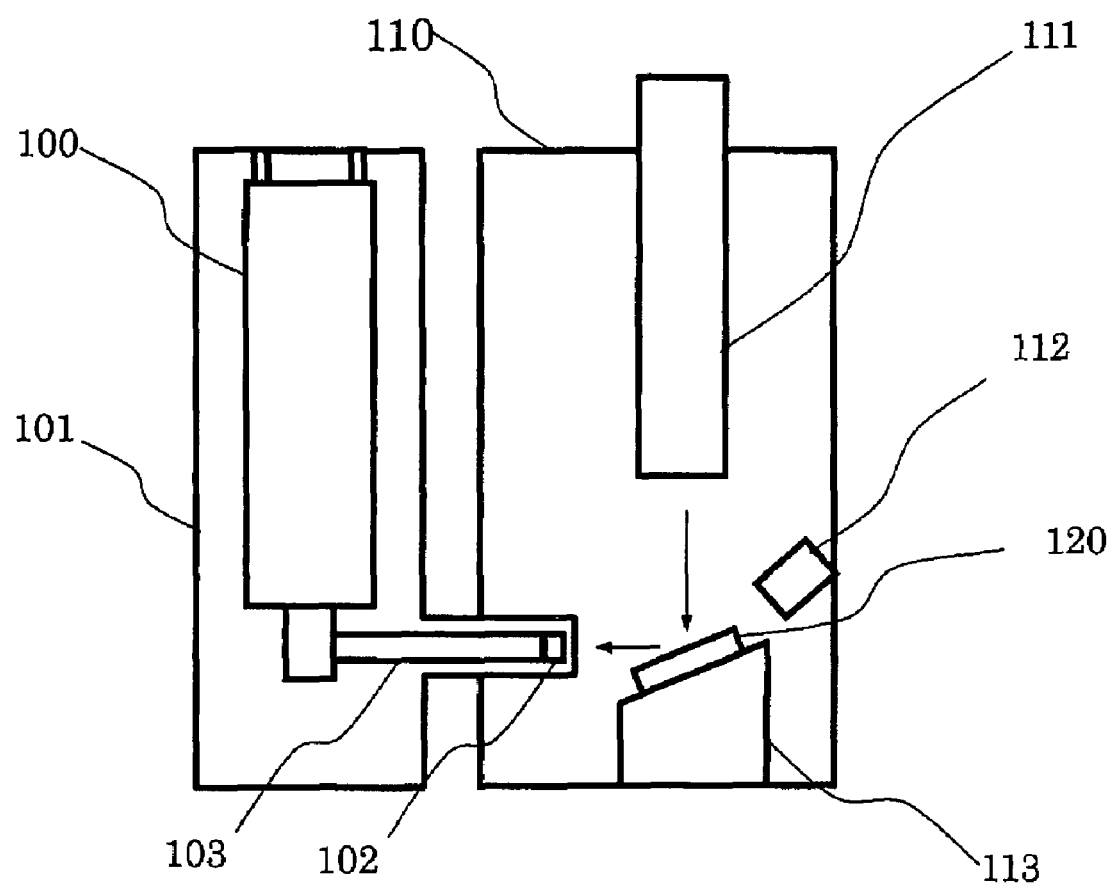
FIG. 5 is an outline view of an X-ray analysis apparatus using a superconducting X-ray detector according to the invention.

FIG. 5 is an outline view showing a constitution of an X-ray analysis apparatus using the superconducting X-ray detector according to the invention. The superconducting X-ray detector 102 is fixed to a front end portion of the cooling head 103 at inside of the cabinet 101 and is inserted to the sample chamber 110 of a scanning type electron microscope (hereinafter, referred to as 'SEM') maintained in a vacuum environment. Further, the sample chamber 110 is installed with the lens-barrel 111 constituted by an electron gun for irradiating an electron beam, an electronic lens for focusing the electron beam and the like, the sample stage 113 for installing the sample 120, the secondary electron detector 112 for detecting electrons generated from the sample 120 and the like.

Further, in order to cool the superconducting X-ray detector 102, the refrigerator 100 is provided at inside of the cabinet 101 constructing at least a portion of providing the cooling head 103 separately from SEM by an adiabatic structure, and the superconducting X-ray detector 102 is fixed to the front end of the cooling head 103.

An X-ray generated from the sample 120 by irradiating the electron beam emitted from the lens-barrel 111 of SEM is detected by the superconducting X-ray detector. The superconducting X-ray detector 102 needs to be installed to be proximate to the sample 120 in order to promote an efficiency of detecting the X-ray.

Further, although according to the embodiment, the example is taken by the scanning type electron microscope for irradiating the electron beam to the sample as a lens-barrel, by irradiating the sample by using a lens-barrel for irradiating ions, an X-ray or the like, an X-ray from the sample may be analyzed.

The invention claimed is:

1. A superconducting X-ray detector comprising:
    a temperature detector comprising a superconducting multilayer thin film for detecting a temperature change by heat generated when X-rays are absorbed, and a heat link for controlling a heat flow amount of generated heat that escapes to a support board;
    wherein the superconducting X-ray detector is constituted by a structure that comprises a superconductor layer disposed above the heat link and an insulating member disposed between the superconductor layer and the temperature detector; and
    wherein the superconductor layer and the temperature detector are connected by a superconducting wiring and are constituted by materials by which superconducting transition temperatures of the superconductor layer and the superconducting wiring are higher than a superconducting transition temperature of the temperature detector.

2. A superconducting X-ray detector comprising:
    a temperature detector comprising a superconducting multilayer thin film for detecting a temperature change by heat generated when X-rays are absorbed, and a heat link for controlling a heat flow amount of generated heat that escapes to a support board;
    wherein the superconducting X-ray detector is constituted by a structure that comprises a superconductor layer disposed above the heat link, an insulating member disposed above the superconductor layer, and the temperature detector disposed above the insulating member; and wherein the superconductor layer and the temperature detector are connected by a superconducting wiring, and the superconductor layer and the superconducting multilayer thin film of the temperature detector are constituted by the same material.

3. An X-ray analysis apparatus comprising:

an analysis apparatus including a sample chamber, a lens-barrel contained in the sample chamber for emitting any of an electron beam, ions, and X-rays, a sample stage and a superconducting X-ray detector for irradiating any of the electron beam, the ions, and the X-rays to a sample and analyzing an energy of an X-ray generated from the sample to thereby identify a composition of the sample;

wherein the superconducting X-ray detector according to claim 1 is used for the superconducting X-ray detector.

4. An X-ray analysis apparatus comprising:

an analysis apparatus including a sample chamber, a lens-barrel contained in the sample chamber for emitting any of an electron beam, ions, and X-rays, a sample stage and a superconducting X-ray detector for irradiating any of the electron beam, the ions, and the X-rays to a sample and analyzing an energy of an X-ray generated from the sample to thereby identify a composition of the sample;

wherein the superconducting X-ray detector according to claim 2 is used for the superconducting X-ray detector.

* * * * *